(12) United States Patent
Young et al.

(10) Patent No.: US 7,508,919 B2
(45) Date of Patent: Mar. 24, 2009

(54) DIAGNOSTIC KIT, DEVICE, AND METHOD OF USING SAME

(76) Inventors: Matthew D. Young, 50 Tanglewood Trail, Santa Cruz, CA (US) 95060; Joseph Caruso, 1211 Monte Vista Dr., Redlands, CA (US) 92373; Max Crigger, 437 W. Sunset Dr., Redlands, CA (US) 92373

( * ) Notice: Subject to any disclaimer, the term of this patent is extended or adjusted under 35 U.S.C. 154(b) by 649 days.

(21) Appl. No.: 11/123,427

(22) Filed: May 6, 2005

(65) Prior Publication Data

US 2006/0251220 A1    Nov. 9, 2006

(51) Int. Cl.
*A61B 6/14* (2006.01)
(52) U.S. Cl. .......................... 378/164; 378/38; 378/170
(58) Field of Classification Search .................. 378/38, 378/154, 164, 168–170, 191, 205, 210; 600/426
See application file for complete search history.

(56) References Cited

U.S. PATENT DOCUMENTS

| | | | |
|---|---|---|---|
| 2,566,998 A * | 9/1951 | Strickman .................... 378/154 |
| 3,547,121 A * | 12/1970 | Cherry ........................ 604/116 |
| 3,770,956 A | 11/1973 | Johnson |
| 3,848,136 A | 11/1974 | Seldin |
| 4,181,859 A | 1/1980 | Vitalini |
| 4,349,917 A | 9/1982 | Moore |
| 4,583,538 A | 4/1986 | Onik et al. |
| 4,838,265 A | 6/1989 | Cosman et al. |
| 4,860,331 A | 8/1989 | Williams et al. |
| 4,918,715 A | 4/1990 | Krupnick et al. |
| 4,985,019 A | 1/1991 | Michelson |
| 4,990,155 A | 2/1991 | Wilkoff |
| 5,015,183 A | 5/1991 | Fenick |
| 5,052,035 A | 9/1991 | Krupnick |
| 5,133,660 A | 7/1992 | Fenick |
| 5,178,146 A | 1/1993 | Giese |
| 5,232,452 A | 8/1993 | Russell et al. |
| 5,260,985 A * | 11/1993 | Mosby ........................ 378/164 |
| 5,306,271 A | 4/1994 | Zinreich et al. |
| 5,368,030 A | 11/1994 | Zinreich et al. |
| 5,415,546 A | 5/1995 | Cox, Sr. |
| 5,448,472 A | 9/1995 | Mushabac |
| 5,690,108 A | 11/1997 | Chakeres |
| RE36,461 E | 12/1999 | Russell et al. |
| 6,122,541 A | 9/2000 | Cosman et al. |
| 6,356,621 B1 | 3/2002 | Furumori et al. |
| 6,470,072 B1 | 10/2002 | Johnson |
| 6,594,878 B2 * | 7/2003 | Kohda ........................ 29/417 |
| 6,658,089 B1 | 12/2003 | Mohr et al. |
| 6,678,353 B2 | 1/2004 | Graumann et al. |
| 6,714,628 B2 | 3/2004 | Broyles et al. |
| 2003/0081732 A1 | 5/2003 | Broyles et al. |
| 2004/0076261 A1 | 4/2004 | Broyles et al. |
| 2004/0103903 A1 | 6/2004 | Falahee |

* cited by examiner

*Primary Examiner*—Edward J Glick
*Assistant Examiner*—Thomas R Artman
(74) *Attorney, Agent, or Firm*—Jerry R. Potts

(57) ABSTRACT

A radiopaque diagnostic kit, tool and method for helping a practitioner define an optimal anatomical location of a patient to perform diagnostic and interventional procedures.

16 Claims, 8 Drawing Sheets

US 7,508,919 B2

DIAGNOSTIC KIT, DEVICE, AND METHOD OF USING SAME

BACKGROUND OF THE INVENTION

1. Field of the Invention

This application relates to radiology imaging tools, and more particularly to a diagnostic kit, radiopaque grid tool and method for performing diagnostic and interventional procedures within a body cavity.

2. Background of Prior Art

The negative effect of improper radiopaque imaging is well known in the prior art. Therefore there is a need for a new and improved radiopaque kit, tool and method for helping to define an optimal intraosseous location for performing diagnostic and interventional procedures within a body cavity.

BRIEF SUMMARY OF THE INVENTION

In a preferred embodiment of the present invention, a diagnostic radiopaque tool, and kit includes a flexible grid of radiopaque strands arranged in a predefined order embedded within a flexible sheet of non radiopaque material, to help a practitioner to determine in precise manner an optimal intraosseous location for performing diagnostic and interventional procedures. According to a novel method of using the tool, the tool is placed within the mouth of a patient overlaying a target anatomical shape to physically cover in three dimensions the specific anatomical feature of interest thereby allowing the tool to be used in a first instances as a diagnostic device and then while still in place in the mouth of a patient as an intervention tool for surgical purposes.

BRIEF DESCRIPTION OF THE DRAWINGS

The above mentioned features and steps of the invention and the manner of attaining them will become apparent, and the invention itself will be best understood by reference to the following description of the preferred embodiment(s) of the invention in conjunction with the accompanying drawings wherein.

DETAILED DESCRIPTION OF THE PREFERRED EMBODIMENTS OF THE INVENTION

Methods, tools and a kit for helping a clinician define an intraosseous location for the purpose of performing a diagnostic or intervention procedure within an oral cavity of a patient are disclosed. The following description is presented to enable any person skilled in the art to make and use the invention. For purposes of explanation, specific nomenclature is set forth to provide a thorough understanding of the present invention. Descriptions of specific applications are provided only as examples. Various modifications to the preferred embodiments will be readily apparent to those skilled in the art, and the general principles defined herein may be applied to other embodiments and applications without departing from the spirit and scope of the invention. Thus, the present invention is not intended to be limited to the embodiments shown, but is to be accorded the widest scope consistent with the principles and features disclosed herein.

Figure 1:
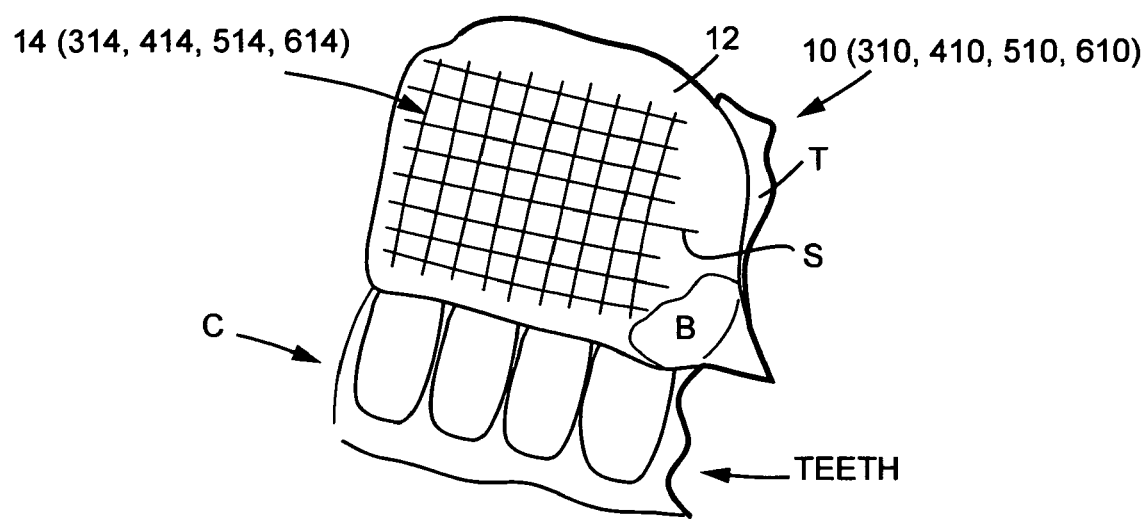
FIG. 1 is a diagrammatic view of a radiopaque procedural tool, which is constructed in accordance with an embodiment of the present invention.

Referring now to the drawings and more particularly to FIG. 1, there is shown a radiopaque grid tool 10, which is constructed according to one of the preferred embodiments of the present invention. The radiopaque grid tool 10 is constructed for utilization by a clinical technician or dental practitioner (not shown) to help define an intraosseous location for the purpose of performing a diagnostic or intervention procedures within an oral cavity C of a patient. As will be explained hereinafter in greater detail, the radiopaque grid tool 10 attaches to the oral cavity surface through the use of a bio-adhesive gel and delivers a topical, local anesthetic at the point of the tool placement, thereby greatly improving patient comfort in preparation for receiving an injection anesthesia with a needle syringe.

Considering now the radiopaque grid tool 10 in greater detail with reference to FIG. 1, the tool 10 generally comprises a sheet of non-radiopaque gel 12 having embedded therein a lattice or grid 14 of radiopaque strands, such as the strand indicated generally at S.

The sheet of gel 12 comprises a viscous polymer bio-adhesive gel, which when set, is sufficiently ridged to hold the grid 14 in fixed placement relative to the gel 12, while simultaneously being sufficiently flexible to lay against and conform to an external shape of a three dimensional object, such as an alveolar bone B in the oral cavity of the patient. In this regard, when the sheet of gel 12 is so conformed to a desired target object (the mucosal tissue T overlying the alveolar bone B), the radiopaque grid 14 will in turn flex as best seen in FIG. 1 and overlay the target object for the purposes of radiopaque imaging. In this manner, when the flexible fixed reference radiopaque grid tool 10 is used in conjunction with a two-dimension or a three-dimensional diagnostic radiographic imaging device (not shown) a clinical technician will be provided with a radiopaque image 210 (FIG. 2) showing a resulting grid image 214 superimposed over a target object image 220. In short, the radiopaque grid tool 10 enables the clinical technician to define an intraosseous location 222 on the grid image in a very convenient and precise manner and then by marking the ideal intersection point 222 on the resulting grid image 214 as a reference point, the technician or practitioner is able to locate the precise intersection point on the tool 10 (which it is still in place at a desired intervention site as best seen in FIG. 1) and then punch through the tool 10 to mark the mucosal tissue T of the patient at a precise intervention location.

In use, as an illustrative example, the radiopaque grid tool 10 helps a clinical technician determine the optimum location for placing a dental implant anchor at a preferred location by selecting an ideal intersection point on the grid tool 10 which precisely locates the widest inter-radicular distance demonstrating the highest bone density at an implant site. Stated otherwise, when the clinical technician views the radiographic image 210 of the intervention site in the mouth of a patient, the strand images of the tool overlay the underlying bone and roots. In this manner the practitioner will be able to easily identify the area of highest bone density and widest root spacing. More specifically, the practitioner will identify which intersection of the grid overlays the area of highest bone density and inter-root spacing.

Figure 10:
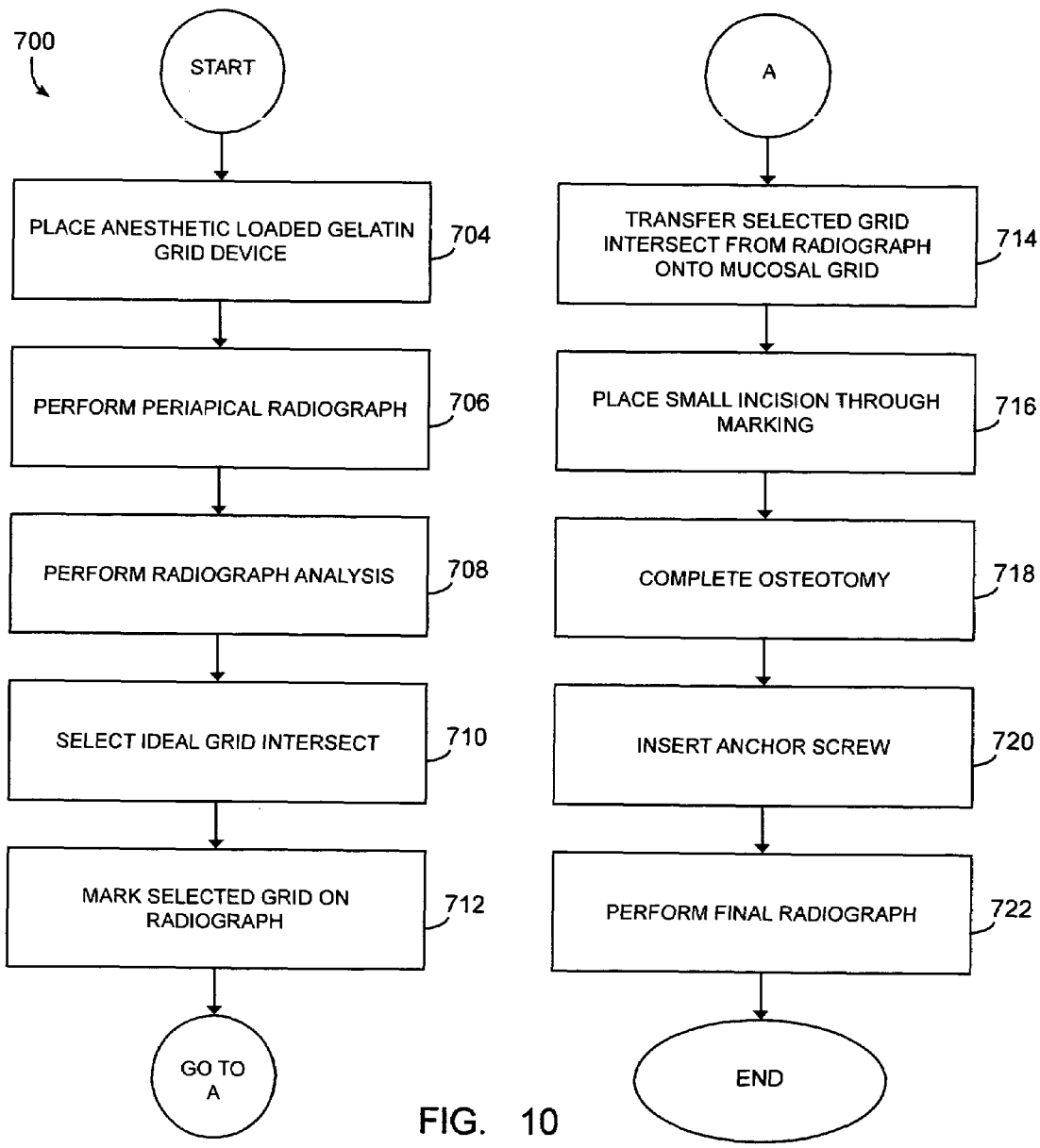
FIG. 10 is a flow diagram of a method of using the radiopaque procedural tool of FIG. 3.

Considering now the use of the tool 10 in greater detail with reference to FIGS. 1 and 10, the practitioner or clinical technician takes the anesthetic-loaded gel radiopaque grid device 10 and in a locating step 704, places the tool 10 onto the mucosal surface location of interest. More specifically, the tool 10 will be placed starting at the gingival margin (the gum line), extending apically (toward the root) without allowing the tool 10 to cover the tool enamel as best seen in FIG. 1 for example. When so placed, the tool 10 self attaches to the target area of interest by non-specific, bio-adhesive physiochemical mechanisms, such as hydrogen bonding and simultaneously delivers a local topical anesthetic embedded within the gel to the target site.

This is an important step in the procedure of using the tool 10, as elaboration will demonstrate. The gel 12 is not a liquid as a liquid denotes a phase of pure compound. A pure compound can exist in several states of matter, including solid, liquid and vapor or gas states. The change in state of the pure compound is effected by a true thermodynamic change. For example, a liquid hardens through an exothermic process and changes phase into a different state of matter, more particularly ice. In this regard, the molecules in the liquid state are in a fluid free flowing form. At the hardening state, the molecules crystallize into an organized, rigid arrangement. The gel 12 does not act in this manner.

The gel 12 is a polymer gel that is a unique non-homogenous material in which the molecules can form network structures either by chemical cross linking or by physical interactions such a electrostatic interactions, hydrogen bonding or physically entanglements. In this regard, gels are irregular, three-dimensional networks of entangled (not crystallized) polymers or colloidal particles that entrap large volumes of liquid, to give the whole structure a "solid-like" characteristic. This network structure results in a dispersion of a liquid throughout a continuous or semi-continuous solid phase. Because of this structure, gel materials have unusual elastic and flow properties, which result in the gel material behaving like neither a classic solid nor a classic liquid. In short, two specific properties that are unique to gels include structure formation and diffusion. Both of these properties are effectively exploited and utilized by the tool 10 as will be explained hereinafter in greater detail.

Considering now the properties and characteristics of the gel material utilized in the sheet 12 in greater detail, gel forming compounds can be derived from natural and synthetic polymers or a combination of both. Bioadhesive gel forming compounds are sold with a wide range of special properties, like molecular weight or gel strength, to suit particular applications.

Natural gelatin powder derived from animal hide and bone is commercially available at most chemical suppliers. Other natural gel forming agents like starch, alginate, pectin, agar, carrageenan etc. are all polymer carbohydrates derived from vegetable sources. These polymer carbohydrates are also commercially available as powders from most chemical suppliers.

The literature demonstrates that a variety of non-natural gel forming polymer compounds have been used for their bioadhesive properties and to improve the bioadhesive properties of natural gel forming compounds. Commercially available polymers such as Carbomers, Carbopol®, hydroxypropyl cellulose, hydroxypropylmethyl cellulose, carboxymethyl cellulose, polyvinylpyrrolidone, and their combinations have been successfully evaluated for their mucoadhesive strength and bioadhesive properties. Other polymers such as polyethylene glycol (PEG) have been successfully evaluated for their ability to control hydration rates in bioadhesive gels to prolong mucosal adhesion.

Several oral adhesive gels are commercially available such as Zilactin®, Oratect® gel, Orabase®, Corsodyl gel®, etc. These commercial formulations could be used with the grid.

Carbomers are commercially available polymer powders that form bioadhesive gels upon dispersion in water. Examples of these powders include Noveon® AA-1 USP, Carbopol® 934 P NF, Carbopol® 971 P NF and Carbopol® 71G NF and Carbopol® 974P.

A specific application is described by sifting gelatin powder (CAS 9000-70-8) into hot (190 F) water at a rate of (20-40 g/100 ml) with constant stirring. The thickened gelatin solution can then be poured into a mold containing the radiopaque grid where initial hardening can occur. The gel increases viscosity at room temperature for 10 minutes. The viscous gel is then covered with a release paper and can be subsequently cut into treatment sections.

Another specific application is to prepare demineralized water, to a pH of 4.5 (pH range 4.0-8.0). The prepared water can be moderately heated (43 C-85 C) to assist in the dissolution process and for lower viscosity gel handling and ease of pouring. Add Noveon® AA-1 USP (0.1-10%) solids in the prepared water under constant stirring. After the polymer particles are dispersed, the gel can be poured into a mold containing the radiopaque grid for initial thickening. The poured gel is then allowed to set for further processing. The viscous gel is then covered with a release paper and can be subsequently cut into treatment sections.

Another specific application well documented in the literature is to mix PEG 400 and PEG 4000 (6:2) in an evaporating dish heated at 70 C and then subsequently cooled to room temperature. The resulting gel can be mixed homogeneously with 0.1-0.2 parts of Carbopol 934P NF and/or 0.2-1 parts polyvinylpyrrolidone. (Tan YTF, Peh KK, Al-Hanbali O. Effect of Carbopol and Polyvinylpyrrolidone on the Mechanical, Rheological, and Release Properties of Bioadhesive Polyethylene Glycol Gels. *AAPS Pharm Sci Tech.* 2000; 1(3): article 24.) The gel solution can then be poured into a mold containing the radiopaque grid. After the gel sufficiently increases in viscosity, the gel can be covered with a release paper and subsequently cut into treatment sections.

Other specific examples applicable to this application are described in prior art U.S. Pat. Nos. 6,290,984 and 6,583,225.

The bioadhesive properties of the gel film are dependent on a variety of factors including film hydration, surface hydration, pH and polymer rheology (viscoelasticity). These variables can be manipulated to achieve an acceptable bioadhesive gel. It is clearly understood that the invention is not limited to any one particular type of gel formulation.

In a preferred embodiment of the present invention, the tool 10 utilizes a collagen protein derived from animals, which is a cold-setting, thermo-reversible gel. In this regard, as noted earlier, when a solution of collagen protein molecules is cooled below a certain temperature, the molecules arrange themselves in a physical entanglement network, such as the structure of gel 12. When such a structure is reheated, the gel once again becomes fluid. The specific formation characteristics of any specific gel depends on several factors, including polymer and liquid type, and relative concentration of the polymer and the liquid. The property of interest in the present invention is gel formation connection to the grid 14 and bio-adhesion. That is, once the grid 14 has been attached with a gel mixture and allowed to set to the desired gel structure properties, it can be removed or replaced with the application of temperature. More specifically, should a dental practitioner need to relocate the tool 10 after its initial placement, the practitioner can easily and quickly do so, simply by the application of heat to the tool 10. This would be true relative to any surface attachment, whether anatomical or inanimate, such as a mucosal surface location or a stent location. It should be understood by those skilled in the art that only a slight temperature change is need to cause the attaching quality of the tool 10 to be sufficiently degraded to allow release of the tool since the gel 12 does not need to go through a true thermodynamic change of state to effect such a change. More specifically, the temperature change required is a function of the amount of time needed to accomplish the heat transfer and the gel tissue interface area. In practice the heat exchange can be accomplished by saturating a clinical sponge, gauze or cloth with heated water (43 C-60 C). The saturated sponge is then placed over the affixed gel and with mild mechanical motion can be worked out of position and removed.

From the foregoing, it should be clear that the attachment mechanism of a gel is distinctly different from the attachment mechanism of a liquid, which must go through an actual state change to be attached to another object.

In short then, the properties of gel 12 can be customized or tailored by polymer and liquid type, and by their specific concentrations to achieve differing levels of attachment as best seen in Table I:

TABLE I

Attachment Characteristic for Different Polymer and Liquid Type Concentrations

| Polymer | Liquid Type | Attachment Characteristic |
|---|---|---|
| Carbopol 971P (0.5% solids) | DI water, pH 5.5 | Viscosity of 4000 to 10,000 cps |
| Carbopol 974P (0.5% solids) | DI water, pH 5.5 | Viscosity of 29,400 to 39,400 cps |
| Gelatin (CAS 9000-70-08) (20-40 g/100 ml) | Water | Adjusting the alpha-chain can affect the gel strength. Viscosity of 3000 to 10,000 cps |

The transmucosal delivery of pharmaceutically active agents to a patient is known. Particularly liposomes, microspheres, nanospheres, biodegradable polymers, and other systems are excellent drug delivery vehicles; and the methods of preparation and drug loading procedures for liposomes and the others are well known in the art. Many of these polymers whether they be natural, synthetic or a combination of the two demonstrate diffusion or transfer behavior through the gel. Liposomal reservoir system bearing local anesthetic benzocaine has been developed for controlled and localized delivery via topical route. The liposomal suspension has been incorporated into an ointment and gel base.

A specific product which is commercially available for this application is Oratect®. This commercial formulation could be used with the grid 14.

The literature demonstrates that 10% wt/wt of lidocaine HCl can be incorporated (prior to the setting and the cutting forming steps that will be described hereinafter in greater detail) into the PEG 400/PEG 4000/Carbopol 934P NF/polyvinylpyrrolidone gel formulation described above.

Other applications are described in the literature include local anesthetics such as lidocaine, procaine, tetracaine, articaine, bupivacaine, mepivacaine or prilocaine, and the pharmaceutically acceptable salts thereof, and steroidal. Specific delivery systems such as those described in prior art U.S. Pat. No. 6,818,224 are suitable delivery systems for use in connection with the grid system. Other applications are described in U.S. Pat. Nos. 6,488,953, 6,635,276, and 6,699,908.

From the foregoing those of ordinary skill in the art will clearly understand that this invention is not limited to any one particular type of delivery formulation.

In summary then, the diffusion property of the gel 12 is qualitatively different than other non-gel liquid solutions including water. In the preferred embodiment of the present invention, the tool 10 is constructed to use the unique diffusion properties of gel, tailored by the specific polymer, liquid and concentrations as shown in Table II, to deliver a topical, local anesthetic at the point of the tool 10 placement. Anesthetic drug release from the gel is governed by a variety of factors, including the volume fraction of water, it's free and bound character, pore size and pore distribution of the gel, interconnections of the network polymer, cross link density and the size of the drug molecules in relation to the gel network molecules.

TABLE II

Diffusion Characteristics for Different Polymer and Liquid Type Concentrations

| Polymer | Liquid Type | Drug | Diffusion Characteristic |
|---|---|---|---|
| Carbopol 971P (0.5% solids) | DI water, pH 5.5 | 10% wt/wt of Lidocaine HCl | Higher diffusion |
| Carbopol 974P (0.5% solids) | DI water, pH 5.5 | 10% wt/wt of Lidocaine HCl | Lower diffusion |
| Carbopol 934P NF/ polyvinylpyrrolidone | PEG 400/ PEG 4000/ Water | 10% wt/wt of Lidocaine HCl | Higher diffusion |

From the foregoing it should there be understood that the physical placement of the tool 10 coupled with the taking of a radiographic image of the tool 10 helps a practitioner define and locate the optimum location to place an implant by physical sight verification when a calibrated tool and visual verification. That is the tool 10 is placed directly over an implant site determined by the practitioner. The adhesion characteristics of the gel 12 allow the gel 12 and the grid 14 to be fixed at the location of interest. Finally, the gel 12 delivers a topical anesthetic to the implant site through the process of diffusion. All of these characteristics of the tool 10 are important features.

After placement of the tool 10 on a desired site location, the practitioner next at a practice step 706 performs a periapical radiograph operation by taking an X-ray picture or image of the site location with the tool 10 in place at the site location.

After the radiograph image is developed, the practitioner at an analysis step 708 performs an analysis of the resulting image which shows the underlying roots and bone structure of the patient with respect to the radiopaque gel grid tool 10. As a result of the visual analysis of the resulting image of the mesh grid superimposed over the underlying bone and tooth root system, the practitioner at an identification or selection step 710, selects an ideal intersection point on the grid 14. That is, the radiograph image of the tool 10 is used by practitioner to determine the optimum location for placing a dental implant anchor, which is generally the widest inter-radicular distance demonstrating the highest bone density. In this regard, the practitioner identifies which intersection of the grid overlays the area of highest bone density and inter-root spacing.

Once the practitioner has identified the grid intersect at the optimum location, the practitioner marks the grid intersect on the radiograph at a marking step 712.

Figure 2:
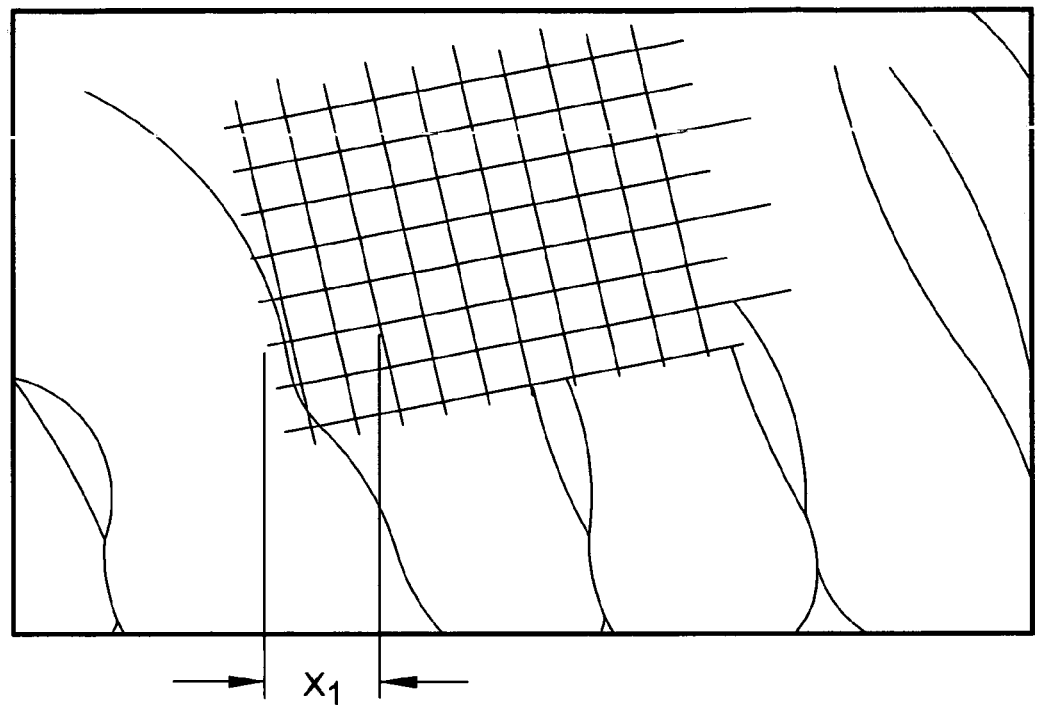
FIG. 2 is a diagrammatic view of a radiograph image of a body cavity target object and another radiopaque procedural tool, which is constructed in accordance with another embodiment of present invention.

Next, the practitioner, using the radiograph with the marked grid intersection as a reference, finds the corresponding intersection point on the grid 14 which is still held in place in mouth of the patient, and marks the grid 14, at a transfer step 714, by using a soft punch to cut a hole in the selected location depicted on the radiograph image, such as the location 222 on the grid image 214 as illustrated in FIG. 2 for example. From the foregoing, it should be understood by those skilled in the art of the importance of the attachment property and the diffusion property of the gel 12. In this regard, the gel 12 holds the grid 14 in its precise location (the exact same location when the radiograph image 210 was taken) while simultaneously continuously delivering the local topical anesthetic to the patient. This, of course, assures the accuracy of locating the drill site for the implant and prepares the site for the surgical procedure that follows while improving the comfort of the patient in preparation for receiving an injection anesthesia with a needle syringe.

After marking the grid 14 at step 714, the practitioner proceeds to an incision step 716, where the practitioner places a small incision through the marking on the grid 14. That is, the practitioner places a surgical knife at the punched grid intersection 222 and makes a small cut through the soft gum tissue to expose the bone. Here again the local anesthetic delivered by the gel 12 provides improved comfort for receiving an anesthetic by a needle syringe.

Next, at a drilling step 718, the practitioner completes the osteotomy by placing a bone drill perpendicular to the marking on the grid 14 and positions the drill bit onto the exposed bone. In this manner, the practitioner is able to drill into the bone to a desired depth, which is a sufficient depth of about the length of the implant anchor. This procedure thus, provides a guide for the implant anchor.

While the guide hole in place, the practitioner next at an insertion step 720, places the implant anchor into the drilled guide hole and screws the anchor tightly into place.

After the implant anchor is securely inserted into the drilled guide hole, the practitioner verifies the placement of the anchor at an imaging taking step 722 by taking a final radiograph to assure proper placement. That is, the practitioner takes a second radiograph image to confirm that the implant anchor was placed at the correct location of high bone density and widest root spacing as determined from the radiograph image 210, for example.

Once the placement of the anchor has been verified, the process comes to an end.

Considering now the diagnostic tool 10 in still greater detail with reference to FIG. 1, the grid 14 of radiopaque strands S are arranged in a predefined order embedded within the flexible sheet 12 of non radiopaque gel material. The sheet 12 and the grid 14 have a sufficient flexibility to flex and conform to an external shape of a three-dimensional anatomical structure but not such a sufficient flexibility to hinder molding of the sheet 12 to the three-dimensional structure.

As best seen in FIGS. 3-6, the grids of the radiopaque tool may be arranged in different configurations. For example, the grids may be arranged with strands of alternating diameters in the X and Y coordinate directions; with strands having uniform diameters and spacing in the X and Y coordinate directions; with strands having a uniform diameter in an X direction of the grid and with another uniform diameter in a Y direction of the grid; and the grid strands have a repeating pattern in one direction only. With respect to this last mentioned arrangement, the one direction only could be either in an X coordinate direction of the grid or a Y coordinate direction of the grid.

It should be understood by one skilled in the art based upon this disclosure that the sheet 12 is a sheet of gel material, which may be configured with customized or tailored diffusion and self-attaching characteristics. It should also be understood that the flexibility characteristic of the tool 10 may also be varied ranging from a semi-ridged construction to a rigid construction. Finally, it should also be understood that the load of topical local anesthetic disposed with the gel may also be customized as well. In short, the diagnostic tool can be custom made for a variety of different situations depending upon the needs of a patient and the practitioner.

Figure 7:
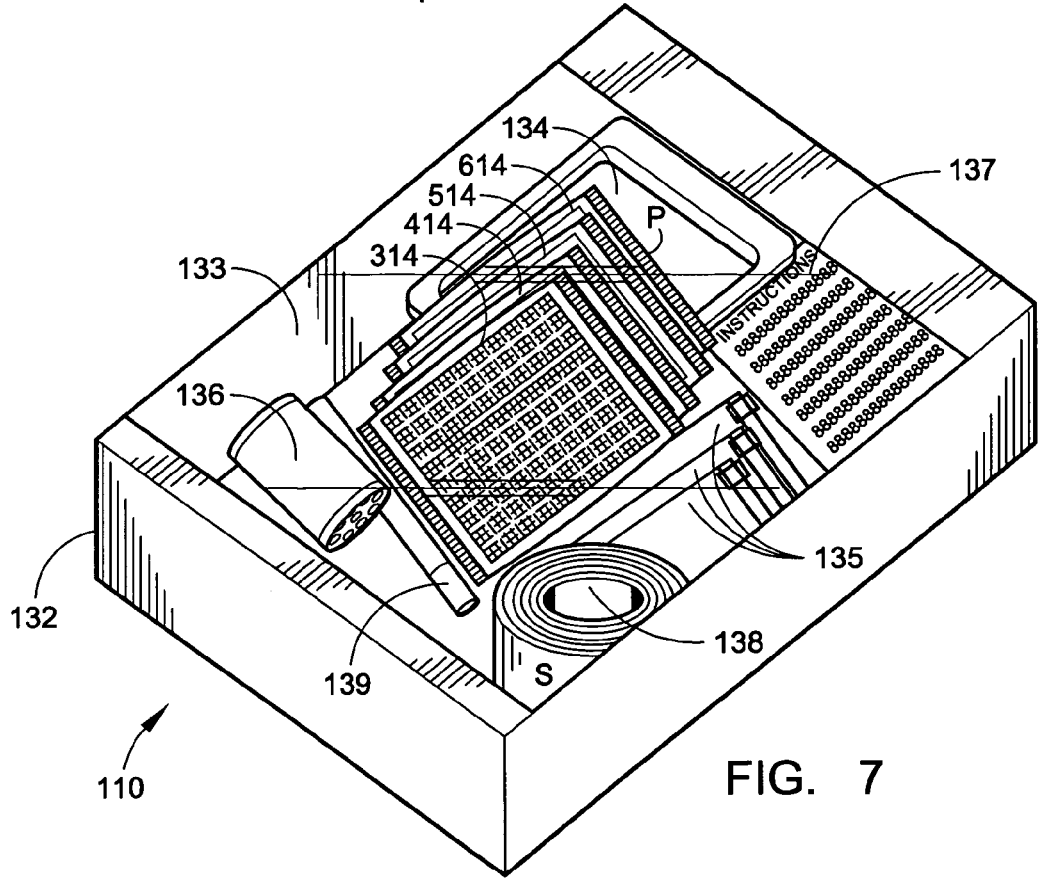
FIG. 7 is a diagrammatic view of a radiopaque procedural tool kit, which is constructed in accordance with another embodiment of the present invention.
Figure 8:
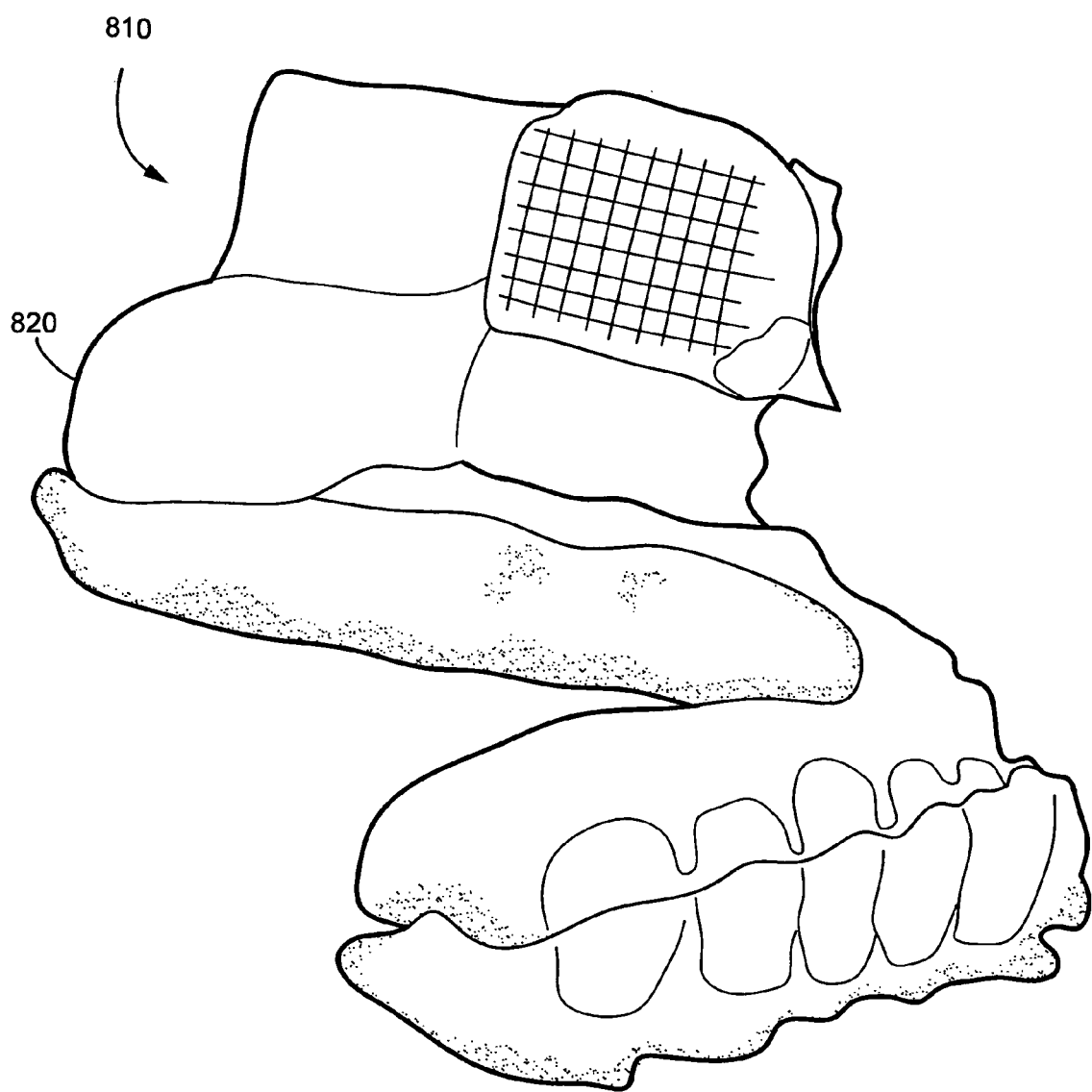
FIG. 8 is a diagrammatic view of a diagnostic and interventional site within the mouth of a patient, illustrating still yet another diagnostic tool, which is constructed in accordance with another embodiment of the present invention.

Referring now to the drawings and more particularly to FIG. 7, there is illustrated a diagnostic tool kit 110 for preparing at least one anesthetic-loaded gelatin radiopaque grid device 10 or alternative at least one surgical stent, such as a surgical stent 850 as illustrated in FIG. 8.

Considering now the tool kit 110 in greater detail with reference to FIG. 7, the tool kit 110 generally comprises a display box 132 with a clear window 133 that allows the clinical technician to clearly see the contents of the kit 110. In this regard, it is contemplated that different kits having different sized grids or grid strand size, will be made available to provide tools with different grid arrangements. For the purpose of clarity, all the grid tools that will be discussed hereinafter in greater detail are identical in structure to grid tool 10 except the tools are provided with different kinds of flexible grids. In should therefore be understood that when reference is made to for example, grid tool 310, the tool itself is identical in physical structure to grid tool 10 but the tool has a different flexible grid arrangement, such as a flexible grid 314. It is for this reason, the grid structure of grid 14 as illustrated in FIG. 1 is generic in nature. Accordingly, when reference is made to grid tool 10, this reference equally applies to grid tool 310 and the other grid tools that will be described hereinafter in greater detail. Similarly, when reference is made to grid 14, this reference equally applies to grid 314 and the other flexible grids that will be described hereinafter in greater detail.

Figure 3:
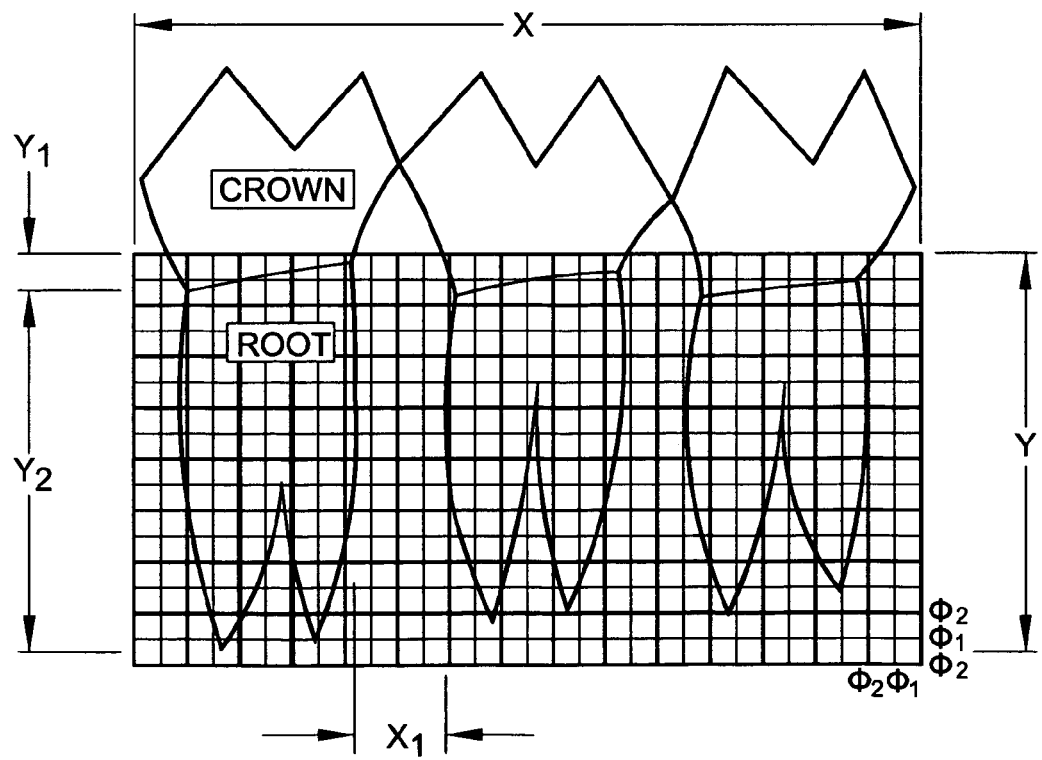
FIG. 3 is diagrammatic view of a radiograph image of yet another radiopaque procedural tool, which is constructed in accordance with another embodiment of the present invention, illustrating the tool superimposed over a radiograph image of another body cavity target object.
Figure 4:
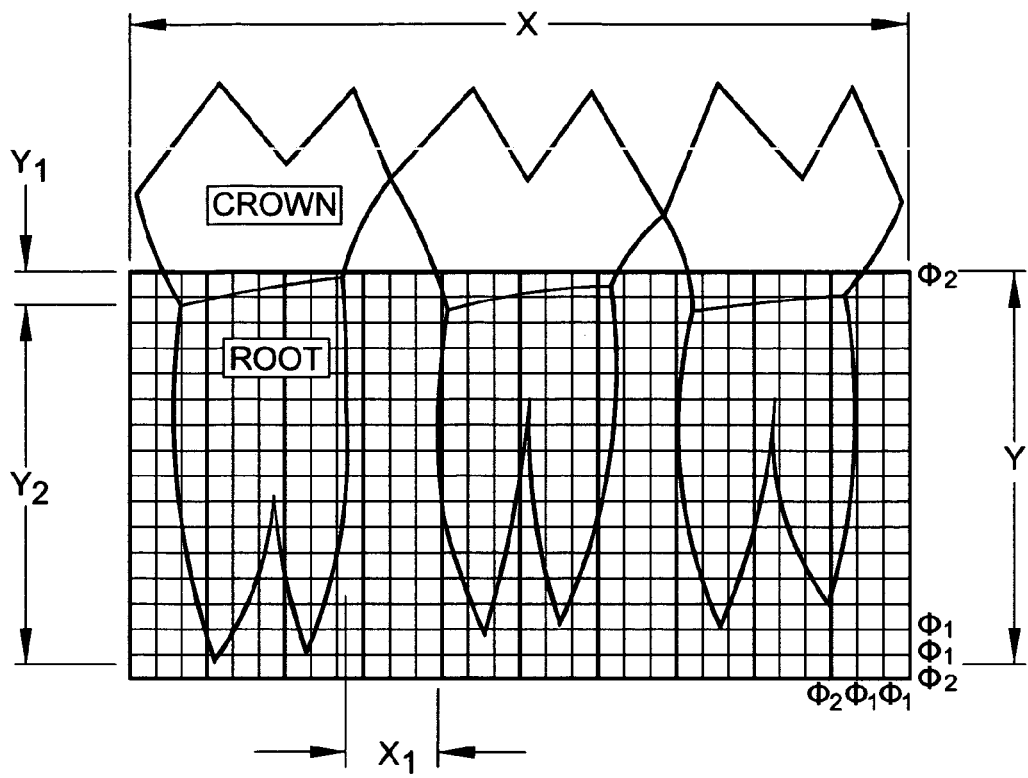
FIG. 4 is diagrammatic view of a radiograph image of still yet another radiopaque procedural tool, which is constructed in accordance with another embodiment of the present invention, illustrating the tool superimposed over the radiograph image of another body cavity target object of FIG. 3.
Figure 5:
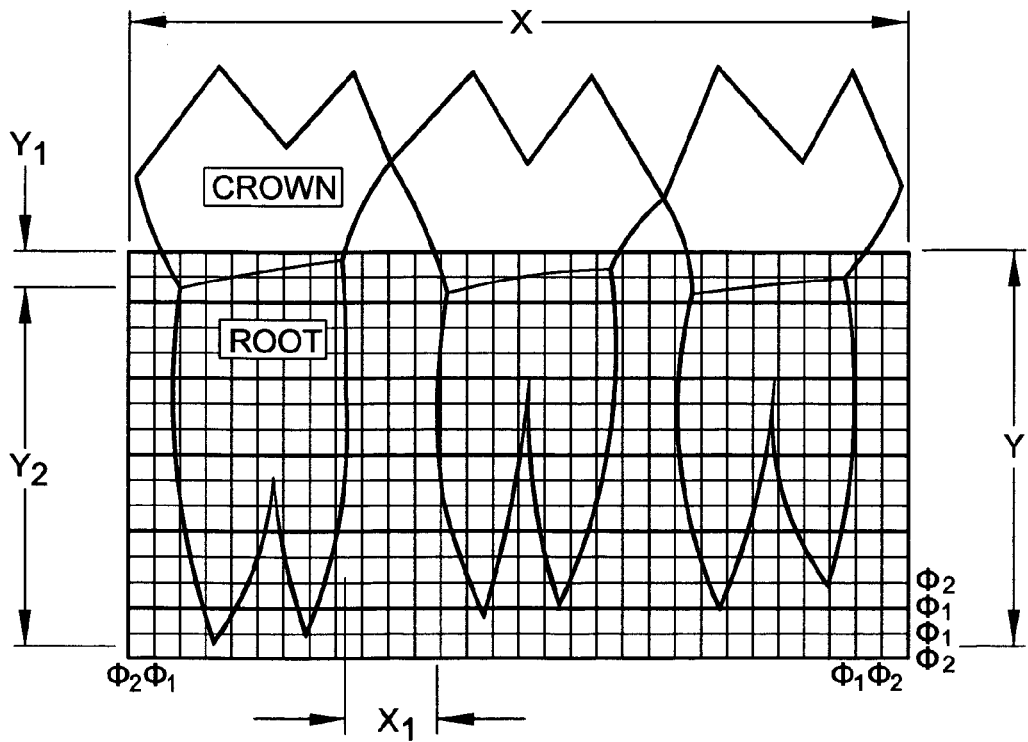
FIG. 5 is diagrammatic view of a radiograph image of still yet another radiopaque procedural tool, which is constructed in accordance with another embodiment of the present invention, illustrating the tool superimposed over the radiograph image of the another body cavity target object of FIG. 3.
Figure 6:
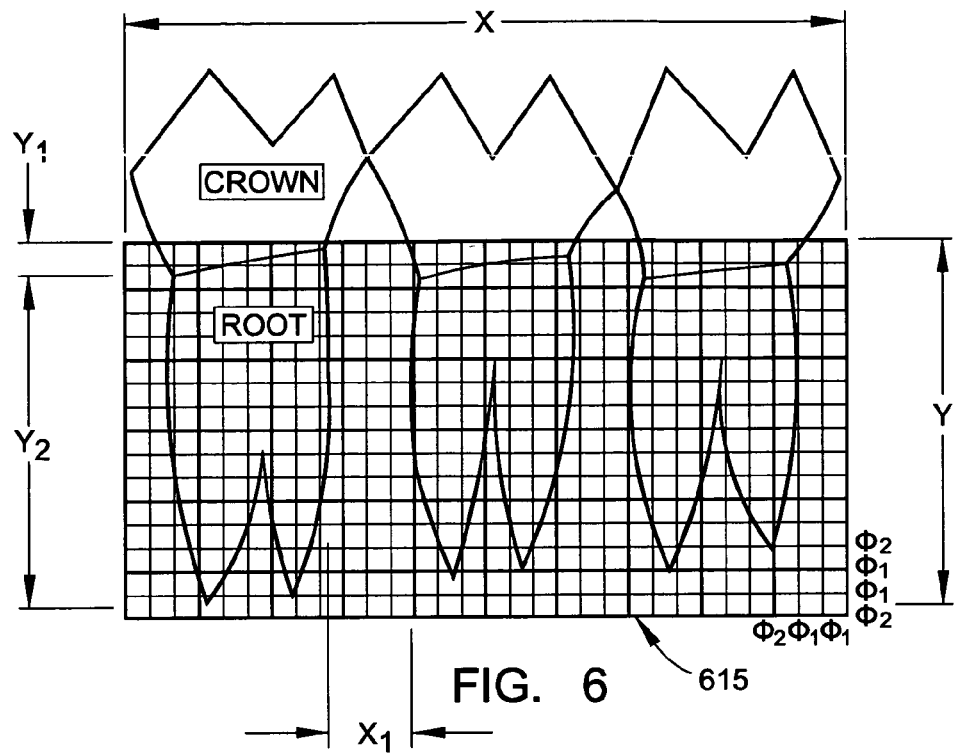
FIG. 6 is diagrammatic view of a radiograph image of still yet another radiopaque procedural tool, which is constructed in accordance with another embodiment of the present invention, illustrating the tool superimposed over the radiograph image of the another body cavity target object of FIG. 3.

Considering again the tool kit 110, the tool kit 110 generally includes a shallow molding tray 134 whose X and Y dimensions are choose to substantially correspond to the X and Y dimensions of grid 314 whose radiograph image 315 is illustrated in FIG. 3. In order to illustrate that tool kits can be provided with different kinds of grids, the tool kit 110 is illustrated with four different packages, where each package contains a different kind of grid arrangement, such as a grid arrangement 414, a grid arrangement 514, a grid arrangement 515, and a grid arrangement 614 where the respective images of the grid 314, 414, 514 and 614 are shown in FIG. 3 (image 314), FIG. 4 (image 415), FIG. 5 (image 515) and FIG. 6 (image 615) respectively.

Although in the preferred embodiment of the present invention the X and Y dimensions of the grids 314, 414, 514, 614, and the tray 134 are substantially identical, it is contemplated that the X and Y dimensions themselves need not be identical. In this case the X dimension may be larger or smaller than the Y dimension and conversely, the Y dimension may be larger or smaller than the X dimension.

As best seen in FIG. 7, the grids 314, 414, 514 and 614 are packaged in different transparent packages or wrappers P to make their identification differences easily seen by the technician. In addition each package P includes indicia (not shown) that also allows for ease in identification.

To help facilitate in the construction of the different kinds of tools (310, 410, 510, and 610) the tool kit 110 also includes a container 136 of a specific kind of polymer gel, a roll of polished paper 138 which has a plurality of tear off sheets, such as the sheet S, an exacta knife 139, a set of storage bags, such as the storage bags 135, and a set of instructions 137 which provides the details for using the kit 110 as will be described hereinafter in greater detail.

Figure 9:
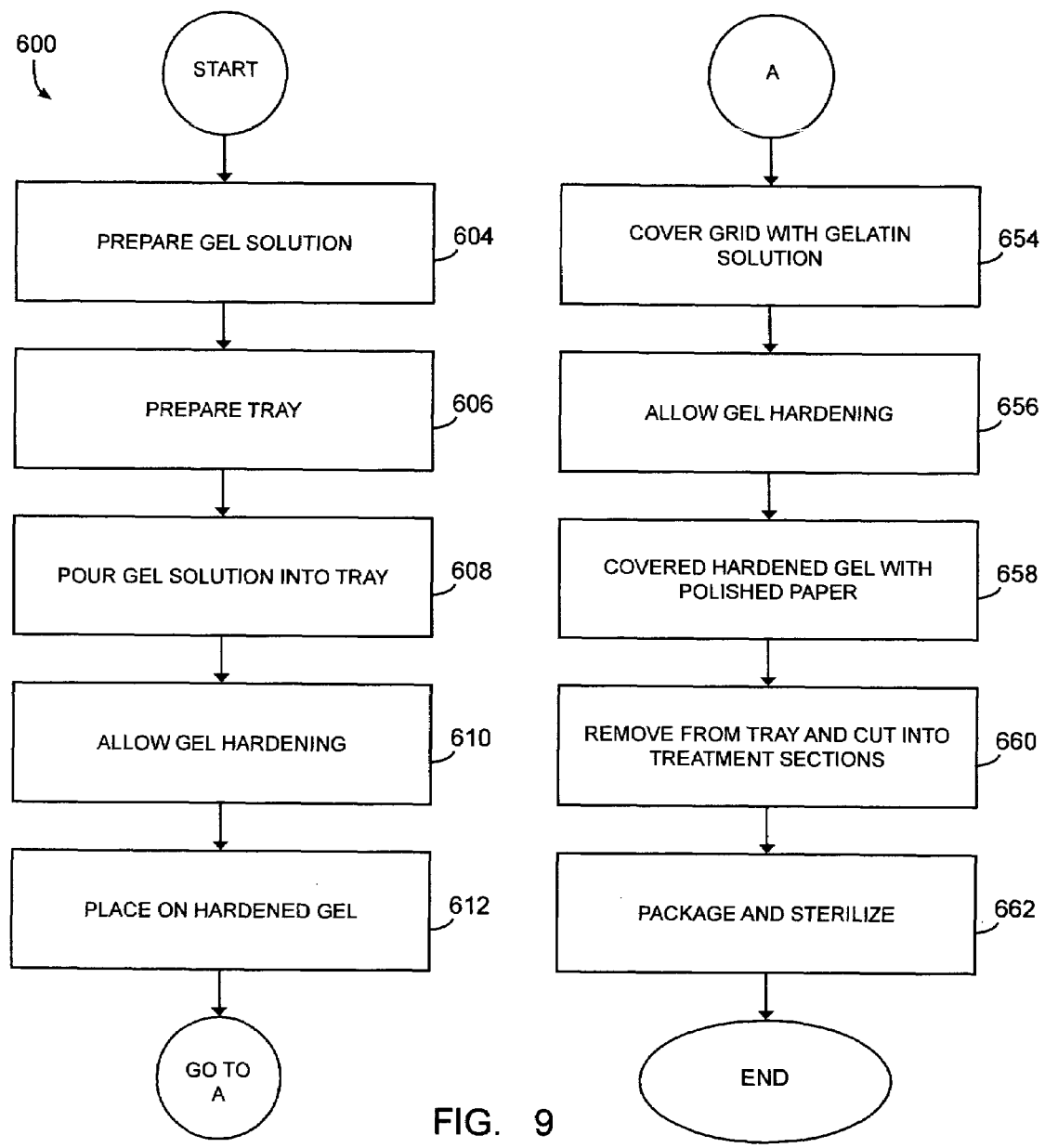
FIG. 9 is a flow diagram of a method of using the radiopaque procedural tool kit of FIG. 7 to construct the radiopaque procedural tool of FIG. 3.

Considering now the method of using the tool kit 110 in greater detail with reference to FIG. 9 for preparing a grid tool, such as the grid tool 310, the user begins at a starting step by opening the package 132 and removing the tray 134, the storage bags 135, the container of polymer gel 136, the set of instructions 137, the polished paper 138, the exacta knife 139, and a bag of the flexible grids, such as the bag with flexible grids 314. The user then proceeds to follow the instructions provided on the instruction sheet 137 by performing the following steps, which are best understood with reference to FIG. 9.

The user begins the process at step 604 by partially fills a measuring container (not shown) with a sufficient amount of warm water to completely cover the bottom of the tray 134 to a depth of about x millimeters, where x is between about 1 mm and about 3 mm. The user then opens the container 136 of polymer gel and measures out a desired amount of the polymer for the tool being constructed and mixes the polymer in water. A topical, local anesthetic is also added to the dispersion, which is then thoroughly mixed so the mixture may be poured into the tray 134 at the appropriate time as will be explained hereinafter in greater detail.

Next the user prepares the tray 134 at step 606. In this regard, the user places the tray 134 on a stationary surface with good lighting and lines the inside shallow surface of the tray with a sheet S of the polished paper separated from the roll 138.

The mixture of water, topical anesthetic and gel prepared at step 604, is then poured into the tray 134 at a pouring step 608.

The viscous gel solution in the tray 134 is then allowed to cool at a cooling step 610 and reach a ridge or semi-ridge state depending upon the desired flexibility characteristic, of the tool 310. In this regard, it takes about ten minutes for the gel to reach its desired state of rigidity.

The user then places one of the grids, such as the grid 314, onto the hardened surface of the gel at a placement step 612. While the gel in the preceding step was being allowed to set, the technician repeated step 604 to have a container holding a solution of the liquid gel, topical anesthetic and water immediately ready. In this regard, immediately after placing the grid 314 on top of the viscous gel, at another pouring step 654, the fluid solution in the holding container is then poured over the grid 314 filling the tray 137 to another sufficient depth of about x millimeters, where x is between about 1 mm and about 3 mm.

The user then allows the gel dispersion to set at step 656, thereby sandwiching the grid 314 between two anesthetic-loaded layers of gel.

Once the viscosity of the gel dispersion has increased sufficiently, at a covering step 658, the user covers the hardened gel with another sheet S of the polished paper separated from the roll 138. The sheets S of polished paper allow for easy in removing the gelatin from the tray 134 and ease in handling the hardened gel once it has been removed from the tray 134.

At a removal step 660, the user turns the tray 134 upside down, which in turn allows the hardened gel to fall or be removed from the tray 134 onto a convenient cutting surface (not shown). Using the exacta knife 139, the user the cuts the sheet of grid bearing gel into desired tool pieces, such as the tool 310. In the preferred embodiment of the present invention, a preferred size for each tool is about 10-20 mm by 10-20 mm.

The individual tool pieces are then packaged at a packaging step 562, into the labeled container packages 135 which are sterile and sealed each package for future use. The precut, pre-gelled, pre-sterilized grids may then be repackaged for future use. While it is entirely possible for a practitioner to use the kit 110 as described, for convenience and easy of use it is contemplated that most practitioners would prefer to use pre-assembled gel grids. In this regard, it is contemplated within the true spirit and scope of the present invention, that at least two different types of pre-assembled grid kits satisfy this need, for example, a pre-assembled gel-grid kit and a pre-assembled stent grid kit. Each of these pre-assembled kits will now be considered in greater detail.

Considering now the gel-grid kit in greater detail, the gel-grid kit generally includes at least two prepackaged gel grid packets, sutures, a suture needle, and other disposable and non-disposable items all packaged in a ready to use state. The disposable items include gauze pads of an appropriate size, such as 2-inch by 2-inch pads, a marker, film, stent, tissues, a scalpel, anchor insertion supplies, anchor implant, drill, abutment and a tapping tool. The non-disposable items include a needle holder, trephine, and a periosteal elevator. Each of the items described with the exception of the gel grid packets are well known to those skilled in the art and therefore they are not described nor shown. It should be sufficient to note that individual kits may be customized for various in office situations, where the most important consideration is that the tool kit is delivered to the practitioner in a ready to use state. In this regard, all a practitioner needs to do, is open the kit package, remove the grid, wet the gel side of the grid and affix it in place over the physical anatomy structure of interest.

Considering now the stent-grid kit in greater detail, the stent-grid kit generally includes at least four prepackaged grid packets (a grid is individually packaged and pre-sterilized), sutures, a suture needle, a vacuform stent, a suitable quantity of an adhesive, and various disposable and non disposable materials, such as those disposable and non disposable materials previously described with reference to the gel-grid kit. In use then, the practitioner opens the package and sandwiches the grid in a radiographic/surgical stent. The stent-grid includes only bare grid strands without the pre-attached gel.

Considering now the various kinds of anesthetic-loaded gel radiopaque grid devices that may be produced from the kit 110, the grid tool 310 whose grid image 315 is best seen in FIG. 3 generally includes a set of strands S which are equally spaced from one another along the X coordinate axis and equally spaced from one another along the Y coordinate axis.

Another grid tool device 410 is similar in construction to grid tool 310 also includes a set of strands S, whose strand images 416 produced from a grid arrangement 414, are likewise equally spaced from one another along the X coordinate axis and equally spaced from one another along the Y coordinate axis. However, in this case predefined intervals along the X coordinate axis, the strand diameter of designated ones of the strands is greater in diameter than those strands adjacent to the strand with the greater diameter. This allows identification of locations along the X-axis to be made easier.

Another grid tool device 410, similar in construction to grid tool 310, includes a set of strands S, whose strand image 416 is produced from a grid arrangement 414. The grid arrangement 414, like grid arrangement 314, includes strands, which are likewise equally spaced from one another along the X coordinate axis and equally spaced from one another along the Y coordinate axis. However, in this case at predefined intervals along the X coordinate axis, the strand diameter of designated ones of the strands in grid 414 are greater in diameter than those strands adjacent to the strand with the greater diameter. This allows identification of locations along the X-axis to be made in a much faster and easier manner.

Yet another grid tool device 510, is also similar in construction to grid tool 310, and includes a set of strands S, whose strand image 516 is produced from a grid arrangement 514. The grid arrangement 514, like grid arrangement 314, includes strands, which are likewise equally spaced from one another along the X coordinate axis and equally spaced from one another along the Y coordinate axis. However, in this case, at predefined intervals along the Y coordinate axis, the strand diameter of designated ones of the strands in grid 514 are greater in diameter than those strands adjacent to the strand with the greater diameter. This allows identification of locations along the Y-axis to be made in a much faster and easier manner.

Still yet another grid tool device 610, is also similar in construction to grid tool 310, and includes a set of strands S, whose strand image 616 is produced from a grid arrangement 614. The grid arrangement 614, like grid arrangement 314, includes strands, which are likewise equally spaced from one another along the X coordinate axis and equally spaced from one another along the Y coordinate axis. However, in this case, at predefined intervals along both the X coordinate axis and the Y coordinate axis, the strand diameter of designated ones of the strands in grid 614 are greater in diameter than those strands adjacent to the strand with the greater diameter. This allows identification of locations along the X-axis and the Y-axis to be made in a much faster and easier manner.

Figure 11:
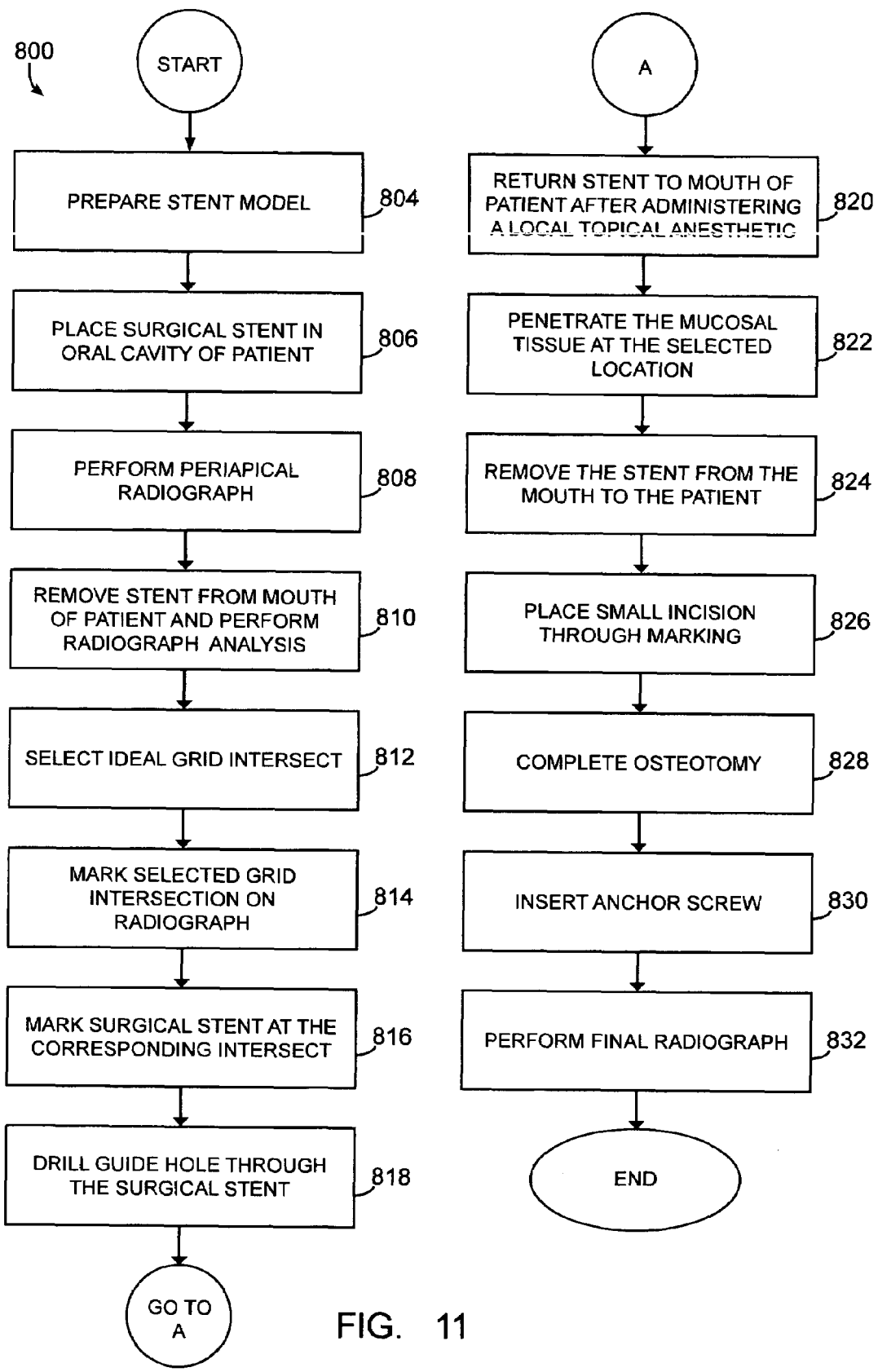
FIG. 11 is a flow diagram of using a surgical stent with the radiopaque procedural tool of FIG. 1.

Referring now to the drawings and more particularly to FIG. 11, there is shown a method 800 of using a flexible grid member, such as a flexible grid member 914 on a surgical stent. The method 800 starts at a stent preparation step 804, when a practitioner prepares an impression of the dental structures within the mouth of a patient. The created negative impression is then filled with cement like material to create a positive model 840 of the dental structure of the patient. Using the positive model, the practitioner then places a radiopaque grid, such as the grid 914, during a placement step 704, onto the model at a location of interest, for example, where an implant is to be placed. The model now becomes a surgical stent 850. More particularly, the mesh grid 914 is placed relative to the model location of the mucosal surface starting at the gingival margin, extending apically, and not covering the model of the tooth enamel area located at about the point of interest.

Once the grid device 914 is placed onto the model 840, the newly created surgical stent 850 is placed once again into the mouth of the patient at a return step 804. In this regard, once the stent has been returned to the mouth of the patient, an acquire image step 808 is performed by the taking of a radiograph. The resulting radiograph image will show a grid image of the grid 914 relative to the underlying root and bone structure of the patient. Based on this image, the practitioner will, analyze the radiograph image at an analysis step 810 to determine the ideal or optimum location for the implant. More specifically at a select step 812, the practitioner will select the ideal grid intersection points for the implant.

Next at a marking step the practitioner will mark the location on the radiograph. Now using the marked radiograph, the practitioner at a stent-marking step 816 will locate the grid intersect point on the hand held stent and mark the actual intersection point with a marker.

The practitioner will then at a drill step 818, take the surgical stent and drill a guide hole through the stent at the marked intersection. The practitioner is now ready to complete the implant operation.

The practitioner now administers a local anesthetic to the implant site location and then returns the surgical stent to the mouth of the patient at a return step 820. When the surgical stent is returned to the mouth of the patient, the practitioner at a penetrate step 822, passes a periodontal through the hole prepared in the stent to contact and then penetrate the mucosal tissues through to the bone.

The surgical stent and probe are then removed from the mouth of the patient at a second removal step 824. The practitioner then completes the process in the same manner as previously described with reference to placing the tool directly in contact with the mucosal tissue of the patient. That is at a step 826 a small incision is made at the puncture mark to expose the underlying bone; at a drill step 828 the practitioner drills a implant placement hole into the bone to complete the osteotomy. Next at an insert step 830 the implant is secured into the implant hole, and then another radiograph is taken at a final radiograph step 832 to verify that the implant is in its proper location.

Various strand diameters and spacing are contemplated within the true spirit and scope of the present invention. It should be noted for example, that an acceptable and quite functionally useful strand diameter and spacing to complement a 10-20 mm±5 mm grid square is a strand having a diameter of about 0.46±0.25 mm with a strand spacing of about 1.6±1 mm.

Although in the preferred embodiment of the present invention, the preparation of the stent model was described using a manual process, an alternative approach could just as well have been utilized which would included fabrication of a vacuum form stent where the flexible grid is sandwiched into a stent model. Thus, the present invention has been described herein with reference to the particular embodiments for particular applications. Those having ordinary skill in the art and access to the present teachings will recognize that additional modifications, applications and embodiments are possible within the true scope and spirit of the description. Accordingly, it is therefor intended by the appended claims to cover any and all such modifications, applications and embodiments within the scope of the present invention.

We claim:

1. A radiopaque tool comprising:
a grid of radiopaque strands arranged in a predefined order embedded within a flexible sheet of non radiopaque material;
wherein said sheet is a gel material with tailored diffusion and self-attaching characteristics;
wherein said sheet is a semi-rigid three-dimensional network of entangled polymer particles having a sufficient volume of a liquid local anesthetic disposed therein for continuously anesthetizing a local anatomical site through a diagnostic interventional medical procedure.

2. The radiopaque tool according to claim 1, wherein said grid and said sheet have a sufficient flexibility to flex and conform to an external shape of a three-dimensional anatomical structure but not such a sufficient flexibility to hinder molding of said sheet to said three-dimensional structure.

3. The radiopaque tool according to claim 2, wherein said sheet is a gel material.

4. The radiopaque tool according to claim 3, wherein said grid is arranged in strands of alternating diameters in an X and Y coordinate direction.

5. The radiopaque tool according to claim 3, wherein said grid is arranged in strands with uniform diameters and spacing in an X and Y coordinate direction.

6. The radiopaque tool according to claim 3, wherein said grid is arranged in strands with spacing in an X and Y coordinate direction and having a uniform diameter in an X direction of said grid and another uniform diameter in a Y direction of said grid.

7. The radiopaque tool according to claim 1, wherein said grid has a repeating pattern in one direction only.

8. The radiopaque tool according to claim 7, wherein said one direction only is in an X coordinate direction of said grid.

9. The radiopaque tool according to claim 7, wherein said one direction only is in a Y coordinate direction of said grid.

10. The radiopaque tool according to claim 1, wherein sheet and said grid have a sufficient flexibility to flex and conform to an external shape of a three-dimensional anatomical structure but not such a sufficient flexibility to hinder molding of said sheet to said three-dimensional structure.

11. The radiopaque tool according to claim 10, wherein said sheet has a sufficient self-attaching characteristic to remain in place during an interventional procedure including marking, probing and drilling procedures.

12. The radiopaque tool according to claim 1, wherein said sheet and said grid are attached to a surgical stent to facilitate a diagnostic and interventional procedure.

13. The radiopaque tool according to claim 1, wherein said grid of radiopaque strands arranged in a predefined order embedded within a flexible sheet of non radiopaque material conform to the shape of a localized area of a surgical stent.

14. A radiopaque tool kit, comprising:
a plurality of flexible grids of radiopaque strands arranged in a predefined order;
a molding tray for holding an individual one of said plurality of flexible grids in a static position;
a container of polymer particles reactive with a liquid; and
a set of instructions for using said tray, an individual one of said flexible grids and a predetermined amount of the polymer particles in said container for forming a self attaching radiopaque diagnostic tool having a certain diffusion characteristic for the continually releasing of an anesthetic liquid during a diagnostic and interventional procedure.

15. The radiopaque tool kit according to claim 14, further comprising:
at least another plurality of flexible grids of radiopaque strands arranged in another predefined order for facilitating the forming of another self-attaching radiopaque diagnostic tool.

16. The radiopaque tool kit according to claim 14, further comprising:
at least another container of polymer particles reactive with a liquid for facilitating the formation of another self attaching radiopaque diagnostic tool having a different self-attaching characteristic than said self-attaching radiopaque diagnostic tool.

* * * * *

UNITED STATES PATENT AND TRADEMARK OFFICE
CERTIFICATE OF CORRECTION

PATENT NO. : 7,508,919 B2
APPLICATION NO. : 11/123427
DATED : March 24, 2009
INVENTOR(S) : Matthew D. Yound, Joseph Caruso and Max Crigger It is certified that error appears in the above-identified patent and that said Letters Patent is hereby corrected as shown below:

Title Page, Item (57) Abstract: line 2, delete "of a patient" and substitute therefor --within a patient in order--.

Column 1, line 30, delete "instances" and substitute therefor --instance--.

Column 3, line 36, delete "tool" and substitute therefor --tooth--.

Column 7, line 6, delete "706" and substitute --706,--.

Column 9, line 40, delete "fills" and substitute therefor --fillings--.

Column 9, line 66, delete "repeated" and substitute therefor --repeats--.

Column 12, line 57, delete "included" and substitute therefor --include--.

Signed and Sealed this

Twenty-third Day of June, 2009

JOHN DOLL
*Acting Director of the United States Patent and Trademark Office*